(12) United States Patent
Sato et al.

(10) Patent No.: US 10,128,538 B2
(45) Date of Patent: Nov. 13, 2018

(54) NON-AQUEOUS ELECTROLYTIC SOLUTION AND LITHIUM ION SECONDARY BATTERY

(71) Applicant: NEC Corporation, Tokyo (JP)

(72) Inventors: Shizuka Sato, Tokyo (JP); Katsumi Maeda, Tokyo (JP); Noriyuki Tamura, Tokyo (JP); Sadanori Hattori, Tokyo (JP)

(73) Assignee: NEC Corporation, Tokyo (JP)

( * ) Notice: Subject to any disclaimer, the term of this patent is extended or adjusted under 35 U.S.C. 154(b) by 125 days.

(21) Appl. No.: 15/324,453

(22) PCT Filed: Jun. 11, 2015

(86) PCT No.: PCT/JP2015/066861
§ 371 (c)(1),
(2) Date: Jan. 6, 2017

(87) PCT Pub. No.: WO2016/006381
PCT Pub. Date: Jan. 14, 2016

(65) Prior Publication Data
US 2018/0183099 A1    Jun. 28, 2018

(30) Foreign Application Priority Data

Jul. 9, 2014    (JP) .................................. 2014-141488

(51) Int. Cl.
*H01M 2/00* (2006.01)
*H01M 10/0567* (2010.01)
(Continued)

(52) U.S. Cl.
CPC ........... *H01M 10/0567* (2013.01); *C07F 9/46* (2013.01); *C07F 9/6568* (2013.01);
(Continued)

(58) Field of Classification Search
CPC ........... H01M 10/0567; H01M 10/052; H01M 10/0525; H01M 10/4235; H01M 10/7011;
(Continued)

(56) References Cited

U.S. PATENT DOCUMENTS

| 5,039,796 A | 8/1991 | Engels et al. |
| 2005/0106458 A1 | 5/2005 | Eguchi et al. |

(Continued)

FOREIGN PATENT DOCUMENTS

| EP | 1487036 A1 | 12/2004 |
| EP | 2683013 A1 | 1/2014 |

(Continued)

OTHER PUBLICATIONS

International Search Report corresponding to PCT/JP2015/066861, 2 pages, dated Sep. 8, 2015.

*Primary Examiner* — Jane J Rhee
(74) *Attorney, Agent, or Firm* — Wilmer Cutler Pickering Hale and Dorr LLP

(57) ABSTRACT

The present invention provides a non-aqueous electrolytic solution comprising a phosphinoamine-based compound represented by formula (1) below and a lithium ion secondary battery comprising the non-aqueous electrolytic solution. By adding the phosphinoamine-based compound to the non-aqueous electrolytic solution, oxidative degradation in the non-aqueous electrolytic solution is suppressed, and thus gas generation is suppressed.

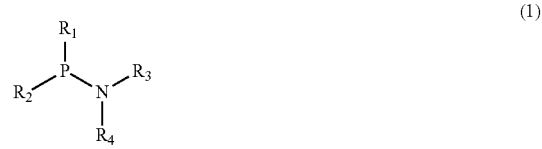

(1)

20 Claims, 1 Drawing Sheet

(51) Int. Cl.
| | |
|---|---|
| *H01M 2/02* | (2006.01) |
| *H01M 4/13* | (2010.01) |
| *H01M 10/052* | (2010.01) |
| *C07F 9/46* | (2006.01) |
| *C07F 9/6568* | (2006.01) |
| *C07F 9/6571* | (2006.01) |
| *H01M 4/131* | (2010.01) |
| *H01M 4/505* | (2010.01) |
| *H01M 4/525* | (2010.01) |
| *H01M 10/0525* | (2010.01) |
| *H01M 10/42* | (2006.01) |
| *H01M 4/02* | (2006.01) |

(52) U.S. Cl.
CPC ...... *C07F 9/6571* (2013.01); *C07F 9/657154* (2013.01); *H01M 2/02* (2013.01); *H01M 2/0287* (2013.01); *H01M 4/13* (2013.01); *H01M 4/131* (2013.01); *H01M 4/505* (2013.01); *H01M 4/525* (2013.01); *H01M 10/052* (2013.01); *H01M 10/0525* (2013.01); *H01M 10/4235* (2013.01); *H01M 2004/028* (2013.01); *H01M 2300/0037* (2013.01); *Y02E 60/122* (2013.01); *Y02T 10/7011* (2013.01)

(58) Field of Classification Search
CPC ........ H01M 2/02; H01M 2/0287; H01M 4/13; H01M 4/131; H01M 4/505; H01M 4/525; H01M 2004/028; H01M 2300/0037
See application file for complete search history.

(56) References Cited

U.S. PATENT DOCUMENTS

| | | |
|---|---|---|
| 2010/0036160 A1 | 2/2010 | Yamamoto et al. |
| 2014/0017573 A1 | 1/2014 | Otsuki et al. |
| 2014/0220426 A1 | 8/2014 | Chernyshov et al. |

FOREIGN PATENT DOCUMENTS

| | | |
|---|---|---|
| EP | 2765135 A1 | 8/2014 |
| JP | S61-208758 A | 9/1986 |
| JP | H06-228172 A | 8/1994 |
| JP | 2003-272643 A | 9/2003 |
| JP | 2008-137979 A | 6/2008 |
| JP | 2012-186009 A | 9/2012 |
| JP | 2014-152174 A | 8/2014 |
| JP | 2014-170689 A | 9/2014 |

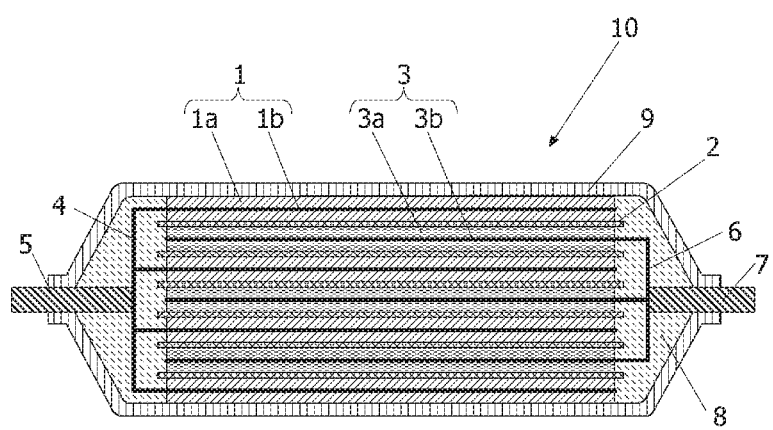

NON-AQUEOUS ELECTROLYTIC SOLUTION AND LITHIUM ION SECONDARY BATTERY

CROSS-REFERENCE TO RELATED APPLICATIONS

This application is a national stage application of International Application No. PCT/JP2015/066861 entitled "NON-AQUEOUS ELECTROLYTIC SOLUTION AND LITHIUM ION SECONDARY BATTERY," filed on Jun. 11, 2015, which claims the benefit of the priority of Japanese Patent Application No. 2014-141488 filed on Jul. 9, 2014, the disclosures of each of which are hereby incorporated by reference in their entirety.

TECHNICAL FIELD

The present invention relates to a non-aqueous electrolytic solution and a lithium ion secondary battery.

BACKGROUND ART

Lithium ion secondary batteries can achieve a high energy density, and thus attract attention as power sources for cellular phones, notebook computers, and the like. Recently, lithium ion secondary batteries have enhanced output characteristics and enhanced long-term reliability such as storage characteristics, and thus also attract attention as power sources for driving the motors of hybrid vehicles (HEVs) and the like. In these applications, it is desired to achieve a higher energy density. In order to enhance the energy density, it is necessary to increase the operating voltage of the lithium ion secondary battery, and a non-aqueous electrolytic solution is desired that does not undergo oxidative degradation even at a high electric potential. For example, the use of an oxidation-resistant solvent or an oxidation-resistance improving additive, a surface treatment of a positive electrode, and the like can be considered as methods for enhancing the oxidation resistance of a non-aqueous electrolytic solution. Also, forming a film on electrodes such as a positive electrode and a negative electrode is a known method for suppressing the oxidative degradation of the non-aqueous electrolytic solution.

For example, Non Patent Literature 1 discloses a technique for adding thiophene to a non-aqueous electrolytic solution. Thiophene is described as forming a film through oxidative polymerization on a positive electrode and being capable of suppressing the degradation of a solvent with the film. Non Patent Literature 2 discloses a technique for suppressing the reaction of a non-aqueous electrolytic solution by inactivating a positive electrode with a phosphorous acid ester. Non Patent Literature 3 discloses a technique for forming a film on a positive electrode with benzene derivatives. Also, Non Patent Literature 4 discloses a technique for forming a film with a phosphoric acid ester.

CITATION LIST

Non Patent Literature

Non Patent Literature 1: Journal of Power Sources 96 (2011) 6997-7001
Non Patent Literature 2: Journal of Power Sources 240 (2013) 471-475
Non Patent Literature 3: Journal of Power Sources 153 (2006) 328-335
Non Patent Literature 4: Journal of the Electrochemical Society 158(3) A337-A342 (2011)

SUMMARY OF INVENTION

Technical Problem

However, none of the above literatures refer to the enhancement of a capacity retention ratio and the suppression of gas generation during operation at a high electric potential. Also, in recent years, there are increasing demands for improving the cycle characteristics of lithium ion secondary batteries.

Accordingly, an object of the present invention is to provide a non-aqueous electrolytic solution capable of obtaining a secondary battery with suppressing gas generation and excellent capacity retention ratio even when high-voltage charge/discharge is performed.

Solution to Problem

One aspect of the present invention is a non-aqueous electrolytic solution comprising a phosphinoamine-based compound represented by the following formula (1):

[Formula 1]

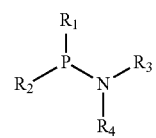

(1)

[In formula (1), $R_1$ and $R_2$ are each independently a hydrogen atom, a substituted or unsubstituted alkyl group, a substituted or unsubstituted alkenyl group, a substituted or unsubstituted cycloalkyl group, a substituted or unsubstituted aryl group, a substituted or unsubstituted heterocyclic group, a substituted or unsubstituted alkoxy group, or a hydroxyl group. $R_3$ and $R_4$ are each independently a hydrogen atom, a substituted or unsubstituted alkyl group, a substituted or unsubstituted alkenyl group, a substituted or unsubstituted cycloalkyl group, a substituted or unsubstituted aryl group, a substituted or unsubstituted heterocyclic group, a substituted or unsubstituted alkoxy group, or a hydroxyl group. $R_1$ and $R_2$ are optionally bonded via a single bond, an ether bond, or a hydrocarbon chain having 1 to 4 carbon atoms. $R_3$ and $R_4$ are optionally bonded via a single bond, an ether bond, or a hydrocarbon chain having 1 to 4 carbon atoms.]

One aspect of the present invention is a lithium ion secondary battery comprising the above non-aqueous electrolytic solution.

Advantageous Effects of the Invention

According to one aspect of the present invention, it can be provided a non-aqueous electrolytic solution capable of obtaining a secondary battery with suppressing gas generation and excellent capacity retention ratio even when high-voltage charge/discharge is performed. According to one aspect of the present invention, it can be also provided a lithium ion secondary battery with suppressing gas generation and excellent capacity retention ratio even when high-voltage charge/discharge is performed.

BRIEF DESCRIPTION OF DRAWING

FIG. 1 is a schematic cross-sectional view showing a configurational example of a lithium ion secondary battery.

DESCRIPTION OF EMBODIMENT

Below, examples of the electrodes and the secondary battery, in which the electrodes can be used, of the present invention will now be described for each component.

[1] Negative Electrode

<Negative Electrode Active Material Layer>

The negative electrode has, for example, a negative electrode active material that is bonded to a negative electrode current collector with a negative electrode binder. In the present exemplary embodiment, any negative electrode active material capable of intercalating and deintercalating lithium can be used as long as the effects of the present invention are not significantly impaired.

There are no other limitations to the negative electrode active material as long as it is capable of intercalating and deintercalating lithium ions, and a known negative electrode active material can be used as desired. For example, carbonaceous materials such as coke, acetylene black, mesophase microbeads, and graphite; lithium metal; lithium alloy such as lithium-silicon and lithium-tin; lithium titanate, and the like can be used. Among these, carbonaceous materials are preferably used in terms of good cycle characteristics and safety and, moreover, excellent continuous-charge characteristics. The negative electrode active material can be used singly, or in combination of two or more thereof.

Moreover, the average particle size ($D_{50}$) of the negative electrode active material is not particularly limited, and from the viewpoint of battery characteristics such as initial efficiency, rate characteristics, and cycle characteristics, it is preferably 1 μm or more and more preferably 15 μm or more, and preferably 50 μm or less and more preferably 30 μm or less. Also, those obtained by coating the above carbonaceous material with organic substance such as pitch and then firing the carbonaceous material, those obtained by forming carbon that is more amorphous than the above carbonaceous material on the surface using a method such as CVD, and the like can also be suitably used as carbonaceous materials. Here, examples of organic substance used for coating include coal tar pitch ranging from soft pitch to hard pitch; coal heavy oils such as dry-distillation liquefied oil; straight-run heavy oils such as atmospheric residual oil and vacuum residual oil; and petroleum heavy oils such as cracked heavy oil (such as Ethylene Heavy End) obtained as a by-product during thermal cracking of crude oil, naphtha, and the like. Also, those obtained by distilling these heavy oils at 200 to 400° C. and grinding the resulting solid residues to 1 to 100 μm can be used. Moreover, a vinyl chloride resin, a phenol resin, an imide resin, and the like can be used. The negative electrode active material layer can be prepared by, for example, roll-forming the above-described negative electrode active material into a sheet electrode or compression-molding it into a pellet electrode, but, normally, as in the case of a positive electrode active material layer, can be prepared by forming a slurry of the above-described negative electrode active material, a binder, and optional various auxiliaries in a solvent as a coating solution, applying the coating solution to a current collector, and drying the solution.

Examples of a negative electrode active material comprising silicon include silicon and a silicon compound. Silicon is, for example, simple silicon. The silicon compound is, for example, silicon oxide, silicate, or a compound of a transition metal and silicon such as nickel silicide or cobalt silicide. The silicon compound has a function of mitigating the expansion and contraction of the negative electrode active material itself caused by repetitive charge/discharge, and is preferably used from the viewpoint of charge-discharge cycle characteristics. Moreover, some kinds of silicon compounds function to ensure conduction through silicon, and from such a viewpoint, the silicon compound is preferably silicon oxide. Silicon oxide is not particularly limited, and is represented by, for example, $SiO_x$ ($0<x<2$). Silicon oxide can contain Li, and Li-containing silicon oxide is represented by, for example, $SiLi_yO_z$ ($y>0$, $2>z>0$). Also, silicon oxide can contain a trace amount of a metal element or a non-metal element. Silicon oxide can contain one element or two or more elements selected from, for example, nitrogen, boron, and sulfur in a proportion of, for example, 0.1 to 5 mass %. Containing a trace amount of a metal element or a non-metal element, silicon oxide can have enhanced electrical conductivity. Also, silicon oxide can be crystalline or amorphous. Also, the negative electrode active material preferably comprises, in addition to silicon or silicon oxide, a carbon material capable of intercalating and deintercalating lithium ions. The carbon material can be incorporated in the state of being a composite with silicon or silicon oxide. As with silicon oxide, the carbon material has functions of mitigating the expansion and contraction of the negative electrode active material itself caused by repetitive charge/discharge and ensuring conduction through silicon that is the negative electrode active material. Accordingly, when silicon, silicon oxide, and the carbon material are concurrently present, better cycle characteristics are obtained.

As the carbon material, for example, graphite, amorphous carbon, diamond-like carbon, a carbon nanotube, or a composite thereof can be used. Here, graphite, which is highly crystalline, is highly electroconductive, and has excellent adhesion to a positive electrode current collector composed of a metal such as copper as well as voltage flatness. On the other hand, amorphous carbon, which has low crystallinity, shows relatively small volume expansion, thus the effect of mitigating the volume expansion of the entire negative electrode is large, and degradation resulting from non-uniformity such as grain boundaries and defects is unlikely to occur. The content of the carbon material in the negative electrode active material is preferably 2 mass % or more and 50 mass % or less, and more preferably 2 mass % or more and 30 mass % or less.

A method for preparing a negative electrode active material including silicon and a silicon compound when silicon oxide is used as the silicon compound is, for example, a method of mixing simple silicon and silicon oxide and sintering the mixture under high temperature and reduced pressure. Moreover, when a compound of a transition metal and silicon is used as the silicon compound, examples include a method of mixing simple silicon and a transition metal and fusing the mixture, and a method of coating the surface of simple silicon with a transition metal by vapor deposition or the like.

In addition to the above-described preparation methods, formation of a composite with carbon can be combined as well. For example, a coating layer composed of carbon can be formed with surrounding the nuclei of simple silicon and silicon oxide by introducing a mixed sintered material of simple silicon and a silicon compound into a gaseous atmosphere of an organic compound in a high-temperature, non-oxygen atmosphere, or by mixing a mixed sintered material of simple silicon and a silicon compound with a carbon precursor resin in a high-temperature, non-oxygen atmosphere. Thereby, further improvement effects are obtained on the suppression of volume expansion caused by charge/discharge and on cycle characteristics.

When silicon is used as the negative electrode active material in the present exemplary embodiment, the negative electrode active material is preferably composed of a composite including silicon, silicon oxide, and a carbon material (hereinafter also referred to as a Si/SiO/C composite). Further, the entirety of or a part of silicon oxide preferably has an amorphous structure. Silicon oxide having an amorphous structure can suppress the volume expansions of the carbon material and silicon that are other negative electrode active materials. Although the mechanism thereof is not clear, it is presumed that the amorphous structure of silicon oxide has a certain influence on the formation of a film on the interface between the carbon material and the electrolytic solution. Also, the amorphous structure is considered to have relatively fewer factors resulting from non-uniformity such as grain boundaries and defects. That the entirety of or a part of silicon oxide has an amorphous structure can be verified by X-ray diffraction measurement (popular XRD measurement). Specifically, when silicon oxide does not have an amorphous structure, peaks specific to silicon oxide are observed, and when the entirety of or a part of silicon oxide has an amorphous structure, the peaks specific to silicon oxide are observed broad.

In the Si/SiO/C composite, the entirety of or a part of silicon is preferably dispersed in silicon oxide. By dispersing at least a part of silicon in silicon oxide, the volume expansion of the negative electrode as a whole can be more suppressed, and the degradation of the electrolytic solution can also be suppressed. That the entirety of or a part of silicon is dispersed in silicon oxide can be verified by using transmission electron microscope observation (popular TEM observation) and energy dispersive X-ray spectroscope measurement (popular EDX measurement) in combination. Specifically, a section of a sample is observed, and the oxygen concentration of silicon portions dispersed in silicon oxide is measured so that it can be verified that the portion is not oxide.

In the Si/SiO/C composite, for example, the entirety of or a part of silicon oxide has an amorphous structure, and the entirety of or a part of silicon is dispersed in silicon oxide. Such a Si/SiO/C composite can be prepared by, for example, a method as disclosed in Patent Literature 3 (JP2004-47404A). That is, the Si/SiO/C composite can be obtained by, for example, performing a CVD treatment on silicon oxide in an atmosphere comprising an organic gas such as methane gas. The Si/SiO/C composite obtained by such a method is in a form that the surface of particles composed of silicon-containing silicon oxide are coated with carbon. Also, silicon is contained in a form of nano-cluster in silicon oxide.

In the Si/SiO/C composite, the proportions of silicon, silicon oxide, and the carbon material are not particularly limited. Silicon is preferably 5 mass % or more and 90 mass % or less and more preferably 20 mass % or more and 50 mass % or less based on the Si/SiO/C composite. Silicon oxide is preferably 5 mass % or more and 90 mass % or less and more preferably 40 mass % or more and 70 mass % or less based on the Si/SiO/C composite. The carbon material is preferably 2 mass % or more and 50 mass % or less and more preferably 2 mass % or more and 30 mass % or less based on the Si/SiO/C composite.

Also, the Si/SiO/C composite can be composed of a mixture of simple silicon, silicon oxide, and a carbon material, and can be prepared by mixing simple silicon, silicon oxide, and a carbon material by mechanical milling as well. For example, the Si/SiO/C complex can be obtained by mixing simple silicon, silicon oxide, and a carbon material each in a particle form. For example, the average particle size of simple silicon can be configured to be smaller than the average particle size of the carbon material and the average particle size of silicon oxide. Accordingly, simple silicon, the volume change of which associated with charge/discharge is large, has a relatively small particle size, and the carbon material and silicon oxide, the volume change of which is small, have a relatively large particle size, and thus dendrite formation and the reduction of the particle size of alloy are more effectively suppressed.

Here, the average particle size of simple silicon can be, for example, 20 μm or less, and is preferably 15 μm or less. Also, the average particle size of silicon oxide is preferably equal to or less than ½ of the average particle size of the carbon material, and the average particle size of simple silicon is preferably ½ or less than the average particle size of silicon oxide. Moreover, more preferably, the average particle size of silicon oxide is equal to or less than ½ of the average particle size of the carbon material, and at the same time the average particle size of simple silicon is equal to or less than ½ of the average particle size of silicon oxide. Controlling the average particle sizes to such ranges makes it possible to effectively obtain the mitigation effect of the volume expansion, and makes it possible to obtain a secondary battery having an excellent balance of energy density, cycle life, and efficiency. More specifically, preferably, the average particle size of silicon oxide is equal to or less than ½ of the average particle size of graphite, and the average particle size of simple silicon is equal to or less than ½ of the average particle size of silicon oxide. Even more specifically, the average particle size of simple silicon can be, for example, 20 μm or less, and is preferably 15 μm or less. Also, a negative electrode active material obtained by treating the surface of the above-described Si/SiO/C composite with a silane coupling agent can be used.

<Binder for Negative Electrode>

A binder for the negative electrode is not particularly limited, and, for example, polyvinylidene fluoride, a vinylidene fluoride-hexafluoropropylene copolymer, a vinylidene fluoride-tetrafluoroethylene copolymer, polytetrafluoroethylene, polypropylene, polyethylene, polyimide, polyamide imide, various polyurethanes, and the like can be used. Among these, polyimide and polyamide imide are preferable because of strong adhesion. Also, an aqueous binder can be used as well. The aqueous binder is not particularly limited, and normally a water-dispersible polymer is used in a latex or emulsion form. For example, an acryl-based resin emulsion, a styrene-based resin emulsion, a vinyl acetate-based polymer emulsion, a urethane-based resin emulsion, and the like can be used. Among these, a water-dispersible synthetic rubber latex or emulsion is preferable in terms of viscoelastic properties. Examples of the water-dispersible synthetic rubber latex (emulsion) include a polybutadiene rubber latex, a styrene-butadiene rubber latex, an acrylonitrile-butadiene rubber latex, a (meth)acrylic acid ester-butadiene rubber latex, and a chloroprene rubber latex. In terms of resistance to the electrolytic solution, a styrene-butadiene rubber latex (SBR latex) is preferable. One of these binders can be used singly, or in combination of two or more thereof. The amount of the binder used is preferably 2 to 10 parts by mass based on 100 parts by mass of the negative electrode active material from the viewpoint of "sufficient binding strength" and "high energy", which are in a tradeoff relationship.

<Thickener for Negative Electrode>

A thickener can also be used to facilitate the preparation of the negative electrode slurry. Examples of such thickeners include carboxymethyl cellulose (including a lithium salt, a sodium salt, and a potassium salt neutralized with an alkali), polyethylene oxide, polypropylene oxide, hydroxyethyl cellulose, hydroxypropyl cellulose, carboxymethyl hydroxyethyl cellulose, polyvinyl alcohol, polyacrylamide, polyhydroxyethyl acrylate, polyammonium acrylate, and polyacrylic acid (including a lithium salt, a sodium salt, and a potassium salt neutralized with an alkali). One of these thickeners can be used singly, or in combination of two or more thereof. The proportion of the thickener in the negative electrode active material layer is preferably 0.1 to 5 mass %.

<Surfactant for Negative Electrode>

When water is used for a dispersion solvent, a nonionic surfactant can also be used to enhance the dispersibility of carbon particles in the slurry. The nonionic surfactant is not particularly limited, and polyoxyalkylene alkyl ether can be preferably used. The polyoxyalkylene alkyl ether is represented by general formula: R—O-(AO)$_n$H (wherein R represents an alkyl group, A represents an alkylene group, and n represents an natural number). Here, there are no particular limitations to the number of carbon atoms of the alkyl group represented by R, the number of carbon atoms of the alkylene group represented by A, and the degree of polymerization of the alkyleneoxy group (AO) represented by n. The polyoxyalkylene alkyl ether can be a mixture of a plurality of polyoxyalkylene alkyl ethers in which at least one of the number of carbon atoms of the alkyl group represented by R, the number of carbon atoms of the alkylene group represented by A, and the degree of polymerization of the alkyleneoxy group (AO) represented by n is different.

<Current Collector for Negative Electrode>

As a material of a current collector for the negative electrode, any known material can be used, and, for example, a metal material such as copper, nickel, or SUS is used. In particular, copper is especially preferable in terms of processing easiness and cost. Also, it is preferable to perform a surface roughening treatment on the current collector in advance. Moreover, the current collector can have any shape, such as a foil shape, a plate shape, or a mesh shape. Also, a perforated current collector such as an expanded metal or a punched metal can be used as well. Also, in the case of using a thin film as a current collector, a preferable thickness and shape can be determined as desired.

<Method for Preparing Negative Electrode>

As for a method for preparing the negative electrode, for example, the negative electrode can be prepared by forming a negative electrode active material layer containing a negative electrode active material, a binder for the negative electrode, a thickener for the negative electrode, a surfactant, and the like on a negative electrode current collector. Examples of a method for forming the negative electrode active material layer include a doctor blade method, a die coater method, a CVD method, and a sputtering method. Alternatively, after forming the negative electrode active material layer in advance, a thin film of aluminum, nickel, or an alloy thereof can be formed by vapor deposition, sputtering, or a like method to provide the negative electrode current collector. In particular, a method including mixing the negative electrode active material, the binder, the thickener, the surfactant, and the like to a dispersion solvent to prepare a slurry, applying the slurry to the current collector, and then thermally drying the slurry enables inexpensive production and is thus preferable. The temperature of thermal drying is preferably 50° C. or higher and 140° C. or lower and, moreover, 80° C. or higher and 120° C. or lower. The dispersion solvent is preferably N-methylpyrrolidone (NMP) or water.

[2] Positive Electrode

<Positive Electrode Active Material Layer>

As a positive electrode active material, an active material that operates at an electric potential of 4.5 V or more versus lithium (hereinafter also referred to as a 5 V class active material) is preferably used from the viewpoint of obtaining a high voltage. Although a gas generation is likely to occur due to the degradation of the components of a non-aqueous electrolytic solution when a 5 V class active material is used, the gas generation can be suppressed and cycle characteristics can be improved by using the non-aqueous electrolytic solution of the present exemplary embodiment. The positive electrode active material that operates at an electric potential of 4.5 V or more versus lithium can be selected by a method as provided below. First, a positive electrode including a positive electrode active material and Li metal are disposed in a battery so as to face each other with a separator therebetween, an electrolytic solution is poured, and a battery is thus prepared. A positive electrode active material that has a charge-discharge capacity of 10 mAh/g or more per mass of the active material at an electric potential of 4.5 V or more versus lithium when charge/discharge is performed at a constant current that provides, for example, 5 mAh/g per mass of the positive electrode active material in the positive electrode can be regarded as the positive electrode active material that operates at an electric potential of 4.5 V or more versus lithium. Also, the charge-discharge capacity per mass of the active material at an electric potential of 4.5 V or more versus lithium when charge/discharge is performed at a constant current that provides 5 mAh/g per mass of the positive electrode active material in the positive electrode is preferably 20 mAh/g or more, more preferable 50 mAh/g or more, and even more preferably 100 mAh/g or more. The shape of the battery can be, for example, a coin type.

The positive electrode preferably includes a 5 V class active material composed of a compound represented by compositional formula $Li_aM1_bO_d$ or $Li_aM1_bM2_cO_d$ (a, b, c, and d indicating the compositional ratio are numerical values in the range of $1.2 \leq a \leq 2$, $0<b$, $c \leq 2$, and and M1 and M2 in the compositional formulae each represent any one of the elements selected from the group consisting of Co, Ni, Mn, Fe, Al, Sn, Mg, Ge Si, and P, provided that M1 and M2 are different elements). In the above formulae, a is more preferably $1.2 \leq a \leq 1.7$. Preferably, M1 and M2 are more preferably selected from Mn, Ni, Co, Fe, P, Mg, Si, Sn, and Al, and even more preferably Mn, Ni, Co, Al, P, or Fe. Preferable specific examples of the compound represented by compositional formula $Li_aM1_bO_d$ or $Li_aM1_bM2_cO_d$ include, but are not limited to, $Li_{1.3}Mn_2O_4$, $Li_{1.2}CoO_2$, $Li_{1.2}NiO_2$, $Li_{1.3}Co_{0.15}Ni_{0.8}Al_{0.05}O_2$, and $Li_{1.3}Mn_{1.5}Ni_{0.5}O_4$.

In addition, for example, lithium manganese composite oxides represented by the following formula (A) can be used as 5 V class active materials:

$$Li_a(M_xMn_{2-x-y}Y_y)(O_{4-w}Z_w) \qquad (A)$$

(In formula (A), $0.4 \leq x \leq 1.2$, $0 \leq y$, $x+y<2$, $0 \leq a \leq 1.2$, and $0 \leq w \leq 1$. M is at least one selected from the group consisting of Co, Ni, Fe, Cr, and Cu. Y is at least one selected from the group consisting of Li, B, Na, Mg, Al, Ti, Si, K, and Ca. Z is at least one selected from the group consisting of F and Cl.)

Also, among such metal composite oxides, spinel-type compounds represented by the following formula (B) are preferably used as 5 V class active materials from the viewpoint of obtaining a sufficient capacity and achieving a long life:

$$LiNi_xMn_{2-x-y}A_yO_4 \qquad (B)$$

(In formula (B), 0.4≤x<0.6, 0≤y<0.3, and A is at least one selected from the group consisting of Li, B, Na, Mg, Al, Ti, and Si.)

In formula (B), 0≤y<0.2 is more preferable.

Also, examples of the active material that operates at an electric potential of 4.5 V or more versus lithium include olivine-type positive electrode active materials. Examples of the olivine-type 5 V active materials include $LiCoPO_4$ and $LiNiPO_4$.

Also, examples of the active material that operates at an electric potential of 4.5 V or more versus lithium include Si composite oxides. Examples of such Si composite oxides include compounds represented by the following formula (C):

$$Li_2MSiO_4 \qquad (C)$$

(In formula (C), M is at least one selected from the group consisting of Mn, Fe, and Co.)

Also, the active material that operates at an electric potential of 4.5 V or more versus lithium can have a layer structure. Examples of 5 V class active materials having a layer structure include compounds represented by the following formula (D):

$$Li(M1_xM2_yMn_{2-x-y})O_2 \qquad (D)$$

(In formula (D), M1 is at least one selected from the group consisting of Ni, Co, and Fe. M2 is at least one selected from the group consisting of Li, Mg, and Al. 0.1<x<0.5, and 0.05<y<0.3)

Lithium metal composite oxides represented by the following formulae (E) to (G) can be preferably used as 5 V class active materials:

$$LiMPO_4 \qquad (E)$$

(In formula (E), M is at least one selected from the group consisting of Co and Ni.)

$$Li(M_yMn_z)O_2 \qquad (F)$$

(In formula (F), 0.1≤y≤0.5, 0.7≥z≥0.33, and M is at least one selected from the group consisting of Li, Co, and Ni.)

$$Li(Li_xM_yMn_z)O_2 \qquad (G)$$

(In formula (G), 0.3>x≥0.1, 0.1≤y≤0.4, 0.7≥z≥0.33, and M is at least one selected from the group consisting of Li, Co, and Ni.)

An electroconductive auxiliary material can be added to the above positive electrode active material layer to lower the impedance of the positive electrode active material. Carbonaceous fine particles such as graphite, carbon black, and acetylene black can be used as electroconductive auxiliary materials.

<Binder for Positive Electrode>

A binder for the positive electrode is not particularly limited, and, for example, polyvinylidene fluoride, a vinylidene fluoride-hexafluoropropylene copolymer, a vinylidene fluoride-tetrafluoroethylene copolymer, styrene-butadiene copolymer rubber, polytetrafluoroethylene, polypropylene, polyethylene, polyimide, and polyamide imide can be used. Among these, polyimide, polyamide imide, polyacrylic acid (including a lithium salt, a sodium salt, and a potassium salt neutralized with an alkali), and carboxymethyl cellulose (including a lithium salt, a sodium salt, and a potassium salt neutralized with an alkali) are preferable because of strong adhesion. The amount of the positive electrode binder used is preferably 2 to 10 parts by mass based on 100 parts by mass of the negative electrode active material from the viewpoint of "sufficient binding strength" and "high energy", which are in a tradeoff relationship.

<Current Collector for Positive Electrode>

A current collector for the positive electrode can be any current collector as long as it supports the positive electrode active material layer containing the positive electrode active material integrated into a single body by a binder and has electrical conductivity that enables conduction with an external terminal, and specifically, the same current collector as the above negative electrode current collector can be used.

<Method for Preparing Positive Electrode>

The method for preparing the positive electrode is not particularly limited, and, for example, only a powder of a surface-treated Mn-based positive electrode, or a powder of a surface-treated Mn-based positive electrode and a powder of a lithium nickel composite oxide, together with an electroconductive auxiliary material and a binder are mixed in a suitable dispersion medium capable of dissolving the binder (a slurry method), then the dispersion is applied to a current collector such as aluminum foil, and the solvent is dried off, followed by compression by a press or the like to form a film. The electroconductive auxiliary material is not particularly limited, and those normally used such as carbon black, acetylene black, natural graphite, artificial graphite, and carbon fiber can be used.

[3] Non-Aqueous Electrolytic Solution

The non-aqueous electrolytic solution of the present exemplary embodiment includes a phosphinoamine-based compound represented by the below-described formula (1). The phosphinoamine-based compound is presumed to function as a film forming agent that forms a film on an electrode. More specifically, by adding the phosphinoamine-based compound to a non-aqueous electrolytic solution, a stable film can be formed on the positive electrode during initial charge/discharge. The film can suppress the oxidative degradation of the components (especially the non-aqueous electrolytic solvent) in the non-aqueous electrolytic solution during charge/discharge (especially during high-voltage charge/discharge), suppress gas generation, and, as a result, enhance the capacity retention ratio. The above mechanism is an assumption, and does not limit the present invention.

[Formula 2]

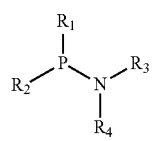

(1)

[In formula (1), $R_1$ and $R_2$ are each independently a hydrogen atom, a substituted or unsubstituted alkyl group, a substituted or unsubstituted alkenyl group, a substituted or unsubstituted cycloalkyl group, a substituted or unsubstituted aryl group, a substituted or unsubstituted heterocyclic group, a substituted or unsubstituted alkoxy group, or a hydroxyl group. $R_3$ and $R_4$ are each independently a hydrogen atom, a substituted or unsubstituted alkyl group, a substituted or unsubstituted alkenyl group, a substituted or unsubstituted cycloalkyl group, a substituted or unsubstituted aryl group, a substituted or unsubstituted heterocyclic group, a substituted or unsubstituted alkoxy group, or a hydroxyl group. $R_1$ and $R_2$ are optionally bonded via a single bond, an ether bond, or a hydrocarbon chain having 1 to 4 carbon atoms. $R_3$ and $R_4$ are optionally bonded via a single bond, an ether bond, or a hydrocarbon chain having 1 to 4 carbon atoms.]

In $R_1$ and $R_2$ of formula (1), the number of carbon atoms of the alkyl group is preferably 1 to 6, more preferably 1 to 4, and even more preferably 1 to 3. The number of carbon atoms of the alkenyl group is preferably 2 to 6, more preferably 2 to 5, and even more preferably 2 to 4. The alkyl group and the alkenyl group can be linear or branched. The number of carbon atoms of the cycloalkyl group is preferably 4 to 7 and more preferably 5 to 6. The number of carbon atoms of the aryl group is preferably 6 to 18, more preferably 6 to 12, and even more preferably 6 to 10. The number of carbon atoms of the heterocyclic group is preferably 2 to 12, more preferably 2 to 10, and even more preferably 2 to 8. The hetero atom of the heterocyclic group is preferably a nitrogen atom, an oxygen atom, or a sulfur atom. The number of carbon atoms of the alkoxy group is preferably 1 to 6, more preferably 1 to 4, and even more preferably 1 to 3. The alkoxy group can be linear or branched.

$R_1$ and $R_2$ can be bonded via a single bond, an ether bond, or a hydrocarbon chain having 1 to 4 carbon atoms to form a cyclic structure. The hydrocarbon chain is preferably a methylene chain that repeats 1 to 3 times. The hydrocarbon chain can be branched. Examples of the ring structure include a structure in which $R_1$ and $R_2$ are both substituted or unsubstituted phenyl groups, and the phenyl groups are bonded to each other via a single bond or an ether bond to form a 5-membered hetero ring or a 6-membered hetero ring, and a structure in which $R_1$ and $R_2$ are both substituted or unsubstituted alkoxy groups, and the alkoxy groups are bonded to each other via a single bond to form a 5-membered hetero ring or a 6-membered hetero ring.

In $R_3$ and $R_4$ of formula (1), the number of carbon atoms of the alkyl group is preferably 1 to 6, more preferably 1 to 4, and even more preferably 1 to 3. The number of carbon atoms of the alkenyl group is preferably 2 to 6, more preferably 2 to 5, and even more preferably 2 to 4. The alkyl group and the alkenyl group can be linear or branched. The number of carbon atoms of the cycloalkyl group is preferably 4 to 7 and more preferably 5 to 6. The number of carbon atoms of the aryl group is preferably 6 to 18, more preferably 6 to 12, and even more preferably 6 to 10. The number of carbon atoms of the heterocyclic group is preferably 2 to 12, more preferably 2 to 10, and even more preferably 2 to 8. The hetero atom of the heterocyclic group is preferably a nitrogen atom, an oxygen atom, or a sulfur atom. The number of carbon atoms of the alkoxy group is preferably 1 to 6, more preferably 1 to 4, and even more preferably 1 to 3. The alkoxy group can be linear or branched.

$R_3$ and $R_4$ can be bonded via a single bond, an ether bond, or a hydrocarbon chain having 1 to 4 carbon atoms to form a cyclic structure. The hydrocarbon chain is preferably a methylene chain that repeats 1 to 3 times. The hydrocarbon chain can be linear or branched.

In formula (1), examples of substituents for $R_1$ to $R_4$ each independently include an optionally branched alkyl group having 1 to 4 carbon atoms (such as a methyl group, an ethyl group, a propyl group, an isopropyl group, or a butyl group), an optionally branched halogen-substituted alkyl group having 1 to 4 carbon atoms (such as a perfluoromethyl group or a perfluoroethyl group), an optionally branched alkoxy group having 1 to 4 carbon atoms (such as a methoxy group, an ethoxy group, a n-propoxy group, an iso-propoxy group, a n-butoxy group, or a tert-butoxy group), an aryl group having 6 to 10 carbon atoms (such as a phenyl group or a naphthyl group), an amino group, a hydroxyl group, or a halogen atom (such as a fluorine atom, a chlorine atom, or a bromine atom). When there is a plurality of substituents on one group, each can be independently different.

The halogen-substituted alkyl group refers to a substituted alkyl group having a structure obtained by substituting at least one hydrogen atom of an unsubstituted alkyl group with a halogen atom (such as a fluorine atom, a chlorine atom, or a bromine atom). The halogen-substituted alkyl group is preferably a fluorine-substituted alkyl group. The fluorine-substituted alkyl group refers to a substituted alkyl group having a structure obtained by substituting at least one hydrogen atom of an unsubstituted alkyl group with a fluorine atom.

The heterocyclic group is preferably a thiophene group from the viewpoint of oxidation resistance.

The phosphinoamine-based compound can be used singly, or in combination of two or more thereof.

The content of the phosphinoamine-based compound in the non-aqueous electrolytic solution is preferably 0.001 mass % or more and 5.0 mass % or less, more preferably 0.01 mass % or more and 2.0 mass % or less, and even more preferably 0.01 mass % or more and 0.3 mass % or less. When the content of the phosphinoamine-based compound is in the above range, a film is easily formed only on the electrode surface, and, also, it is possible to suppress the film becoming excessively thick. As a result, an increase of the internal resistance of the electrode is suppressed, ion conductivity and electron conductivity in the electrode are enhanced, and battery characteristics are enhanced.

Preferable examples of the phosphinoamine-based compound include compounds (PN-1) to (PN-8) below. Among these, compound (PN-1) is more preferable. The phosphinoamine-based compound in the present exemplary embodiment is not limited to these examples.

[Formula 3]

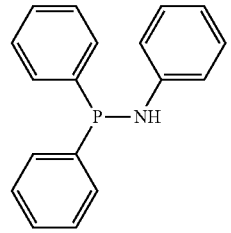

(PN-1)

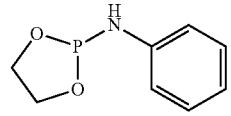

(PN-2)

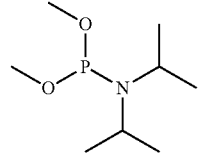

(PN-3)

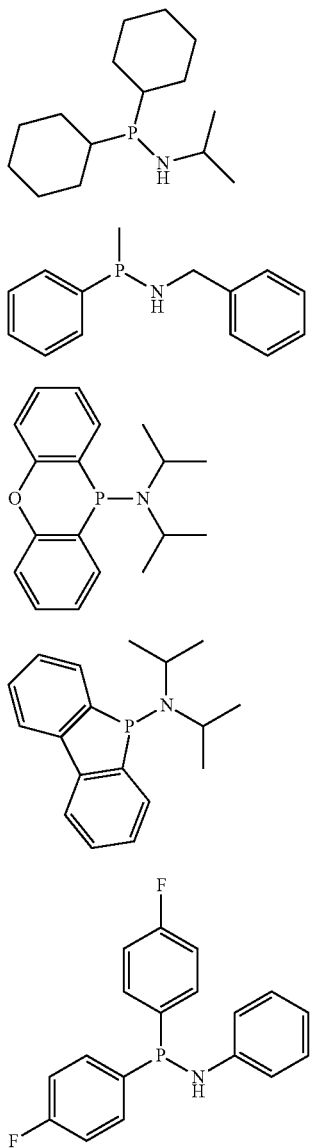

(PN-4)
(PN-5)
(PN-6)
(PN-7)
(PN-8)

Examples of non-aqueous electrolytic solvents contained in the non-aqueous electrolytic solution include one or more kinds selected from the group consisting of, for example, cyclic carbonates, chain carbonates, aliphatic carboxylates, γ-lactones, cyclic ethers, chain ethers, and fluorine derivatives thereof. Specific examples of the non-aqueous electrolytic solvents include cyclic carbonates such as propylene carbonate (PC), ethylene carbonate (EC), and butylene carbonate (BC); chain carbonates such as dimethyl carbonate (DMC), diethyl carbonate (DEC), ethyl methyl carbonate (EMC), and dipropyl carbonate (DPC); aliphatic carboxylates such as methyl formate, methyl acetate, and ethyl propionate; γ-lactones such as γ-butyrolactone; chain ethers such as 1,2-diethoxyethane (DEE) and ethoxymethoxyethane (EME); cyclic ethers such as tetrahydrofuran and 2-methyltetrahydrofuran; dimethylsulfoxide, 1,3-dioxolan, formamide, acetamide, dimethylformamide, acetonitrile, propionitrile, nitromethane, ethyl monoglyme, phosphoric acid triesters, trimethoxymethane, 1,3-dimethyl-2-imidazolidinone, 3-methyl-2-oxazolidinone, propylene carbonate derivatives, tetrahydrofuran derivatives, ethyl ether, and N-methylpyrrolidone. These can be used singly, or in a mixture of two or more thereof.

The non-aqueous electrolytic solution can contain a lithium salt as an electrolyte salt. Examples of the lithium salt include a lithium imide salt, $LiPF_6$, $LiBF_4$, $LiAsF_6$, $LiSbF_6$, $LiClO_4$, $LiAlCl_4$, and $LiN(C_nF_{2n+1}SO_2)(C_mF_{2m+1}SO_2)$ (n and m are natural numbers). These can be used singly, or in a mixture of two or more thereof. Also, in particular, $LiPF_6$ or $LiBF_4$ is preferably used. The use of these makes it possible to increase the electroconductivity of the lithium salt and further enhance the cycle characteristics of the secondary battery.

[4] Separator

The separator is not particularly limited, and a porous film or a non-woven fabric of polypropylene, polyethylene, or the like can be used. Also, a laminate thereof can be used as a separator as well.

[5] Casing

The casing is not particularly limited, and, for example, a laminate film can be used. A laminate film that is stable to the electrolytic solution and has sufficient water-vapor barrier properties can be suitably selected.

In the case of conventional secondary batteries for which a laminate film is used as a casing, the deformation of an electrode element is significantly larger when gas is generated than in secondary batteries for which a metal can is used as a casing. This is because the laminate film is more easily deformed by the internal pressure of a secondary battery than the metal can. Moreover, when sealing a secondary battery for which a laminate film is used as a casing, normally the inner pressure of the battery is made lower than atmospheric pressure, thus there is no extra space inside, and gas if generated may immediately lead to the volume change of the battery and the deformation of the electrode element.

With the secondary battery according to the present exemplary embodiment, gas generation is suppressed even when high-voltage charge/discharge is performed, and as a result, the above problems can be overcome. Accordingly, it is possible to provide a laminate-type lithium ion secondary battery that is inexpensive and provides higher degrees of freedom in designing the cell capacity through changing the number of laminated layers.

As for the laminate film, for example, a laminate film of polypropylene, polyethylene, or the like that is coated with aluminum, silica, or alumina can be used as a casing. In particular, from the viewpoint of suppressing volume expansion, an aluminum laminate film is preferable.

Also, a representative example of the layer configuration of the laminate film is a configuration in which a metal thin film layer and a heat-fusible resin layer are laminated. Also, another representative example of the layer configuration of the laminate film is a configuration in which a protective layer composed of a film of polyester such as polyethylene terephthalate or nylon is laminated on the other surface of the metal thin film layer from the heat-fusible resin layer. When sealing battery components, the battery components are surrounded such that the heat-fusible resin layers face inward. As the metal thin film layer, for example, a foil of Al, Ti, Ti alloy, Fe, stainless steel, Mg alloy, or the like having a thickness of 10 to 100 μm is used. The resin used for the heat-fusible resin layer is not particularly limited as long as it is heat-fusible. For example, polypropylene, polyethylene, acid modified products thereof, polyphenylene sulfide, polyester such as polyethylene terephthalate, polyamide, ethylene-vinyl acetate copolymer, or ionomer resin obtained by causing ethylene-methacrylic acid copolymer or an ethylene-acrylic acid copolymer to have intermolecular bonding with metal ions is used as the heat-fusible resin layer. The thickness of the heat-fusible resin layer is preferably 10 to 200 μm and more preferably 30 to 100 μm.

[6] Battery Configuration

The configuration of the secondary battery is not particularly limited, and, for example, can be a laminate-type that an electrode assembly in which a positive electrode and a negative electrode are disposed to face each other and an electrolytic solution are enclosed within a casing. FIG. 1 is a schematic cross-sectional view showing the structure of a laminate-type secondary battery 10. In the secondary battery 10, a plurality of positive electrodes 1 and a plurality of negative electrodes 3 having a planar structure alternately stacked with a separator 2 therebetween constitute an electrode assembly (also referred to as an electrode element). As for positive electrode current collectors 1b of the respective positive electrodes 1, the ends not covered with positive electrode active material layers 1a are welded to each other to be electrically connected, and, moreover, a positive electrode terminal 4 is welded to the welded portions. As for negative electrode current collectors 3b of the respective negative electrodes 3, the ends not covered with negative electrode active material layers 3a are welded to each other to be electrically connected, and, moreover, a negative electrode terminal 6 is welded to the welded portions. Moreover, the positive electrode terminal 4 is welded to a positive electrode tab 5, and the negative electrode terminal 6 is welded to a negative electrode tab 7. An electrode element having such a planar laminate structure does not have a portion where the radius is small (a region close to the winding core of a winding structure), and is thus advantageous by being less likely to be adversely affected by the volume change of electrodes associated with charge/discharge than an electrode element having a winding structure. That is to say, it is effective as an electrode assembly in which an active material that is likely to undergo volume expansion is used. On the other hand, the electrodes are bent in an electrode element having a winding structure, and thus the structure thereof is likely to be deformed when a volume change occurs. In particular, when a negative electrode active material such as silicon oxide, the volume change of which associated with charge/discharge is large, is used, the capacity reduction associated with charge/discharge of a secondary battery in which an electrode element having a winding structure is used is large. The electrode assembly is enclosed within a casing 9 together with a non-aqueous electrolytic solution 8, and the positive electrode tab 5 and the negative electrode tab 7 extend from the casing 9 to the outside.

However, an electrode element having a planar laminate structure has a problem in that when gas is generated between electrodes, the generated gas is likely to stay between the electrodes. This is because in the case of an electrode element having a winding structure, the distance between the electrodes is unlikely to increase due to the tension exerted on the electrodes, while in the case of an electrode element having a laminate structure, the distance between the electrodes is likely to increase. This problem is particularly prominent when the casing is an aluminum laminate film.

In the present invention, the above problem can be solved by forming a film on a positive electrode with a film forming agent.

Accordingly, the secondary battery of the present exemplary embodiment relates to a laminate-type secondary battery involving an electrode assembly in which a positive electrode and a negative electrode are disposed to face each other, a non-aqueous electrolytic solution, and a casing enclosing the electrode assembly and the non-aqueous electrolytic solution. Also, the positive electrode has a positive electrode active material layer including a positive electrode active material and a positive electrode binder, and a film of the above film forming agent is formed on the positive electrode active material layer.

EXAMPLES

Below, the present invention will now be described more specifically by way of Examples. The present invention is not limited thereto.

Example 1

[Preparation of Negative Electrode]

Silicon having an average particle size of 5 μm, amorphous silicon oxide ($SiO_x$, $0<x\leq2$) having an average particle size of 13 μm, and graphite having an average particle size of 30 μm were weighed to have a mass ratio of 29:61:10. These materials were mixed for 24 hours by so-called mechanical milling to obtain a negative electrode active material (a Si/SiO/C composite). In this negative electrode active material, silicon is dispersed in silicon oxide ($SiO_x$, $0<x\leq2$).

Then, 80 parts by mass of the Si/SiO/C composite, 15 parts by mass of polyimide, and 5 parts by mass of a carbon-based electroconductive auxiliary were mixed, and the mixture was dispersed in N-methylpyrrolidone (NMP) to prepare a negative electrode slurry. Thereafter, the negative electrode slurry was applied to copper foil as a negative electrode current collector such that the thickness after drying was 50 μm, and dried, and the foil was punched out to a size of 23 mm×25 mm to prepare a negative electrode.

[Production of Positive Electrode]

First, 92 parts by mass of a mixture (a 5 V class active material) of lithium nickel manganese cobalt composite oxide and lithium manganese spinel, 4 parts by mass of a carbon-based electroconductive agent, and 4 parts by mass of polyvinylidene fluoride were mixed, and the mixture was dispersed in NMP to prepare a positive electrode slurry. Thereafter, the positive electrode slurry was applied to aluminum foil as a positive electrode current collector such that the thickness after drying was 170 μm, and dried, and the foil was punched out to a size of 22 mm×24 mm to prepare a positive electrode.

[Preparation of Non-Aqueous Electrolytic Solution]

Compound (PN-1) was added such that the content was 0.1 mass % to an ethylene carbonate/diethyl carbonate mixed solution (a mixing ratio (volume-based) of 3:7) containing 1.0 mol/L of $LiPF_6$ as an electrolyte salt to prepare a non-aqueous electrolytic solution.

[Preparation of Small Cell]

The above negative electrode, a polypropylene porous film separator, and the above positive electrode were laminated in this order to obtain an electrode assembly. This electrode assembly was wrapped in an aluminum laminate film, the above non-aqueous electrolytic solution was poured into the film, and then the film was hermetically sealed to prepare a sheet-like lithium ion secondary battery.

[Evaluation]

<Cycle Test>

Charge/discharge of the prepared lithium ion secondary battery was repeated 10 times in a thermostatic chamber at 20° C. in a voltage range of from 1.5 V to 4.5 V to measure the discharge capacity (at the beginning, after 10 cycles). The capacity retention ratio was the proportion (%) of the discharge capacity after 10 cycles relative to the initial discharge capacity. The discharge capacity is a value per unit mass of the positive electrode active material. The result of measuring the capacity retention ratio is shown in Table 1.

<Amount of Generated Gas, Volume Expansion Ratio>

The amount of generated gas was determined by measuring in water the difference between the masses of the lithium ion secondary battery before and after the cycle test and dividing the mass difference by the specific gravity of water. The volume expansion rate was the proportion (%) of the amount of generated gas in the secondary battery prepared in Example 1 relative to the amount of generated gas in the secondary battery prepared in Comparative Example 1, which will be described below.

Comparative Example 1

A lithium ion secondary battery was prepared and evaluated in the same manner as in Example 1 except that the non-aqueous electrolytic solution was prepared without adding compound (PN-1).

TABLE 1

|  | Additive | | Initial discharge capacity (mAh) | Discharge capacity after 10 cycles (mAh) | Capacity retention ratio (%) | Amount of generated gas (cm³) | Volume expansion ratio (%) |
|---|---|---|---|---|---|---|---|
|  | Kind | Content (mass %) | | | | | |
| Example 1 | PN-1 | 0.1 | 37.8 | 28.4 | 75 | 0.35 | 34 |
| Comparative Example 1 | — | — | 36.5 | 25.0 | 68 | 1.02 | 100 |

As shown in Table 1, it was confirmed that, by adding a phosphinoamine-based compound, the cycle characteristics in high-voltage charge/discharge of a lithium ion secondary battery can be enhanced and gas generation can be suppressed.

INDUSTRIAL APPLICABILITY

The present exemplary embodiment can be utilized in, for example, any industrial field where a power source is required and industrial field relating to the transport, storage, and supply of electrical energy. Specifically, it can be utilized for power sources of mobile devices such as cellular phones and notebook computers; power sources of movement/transport media such as trains, satellites, and submarines, including electric vehicles such as electric automobiles, hybrid cars, electric motorcycles, and electrically assisted bicycles; backup power sources such as UPSs; power storage facilities that store electric power produced by solar power production, wind power production, and the like; etc.

The present invention has been described above in reference to an exemplary embodiment and Examples, but the present invention is not limited to the above exemplary embodiment and Examples. Various modifications can be made to the configurations and details of the present invention within the scope of the present invention as can be understood by those skilled in the art.

The present application claims priority to Japanese Patent Application No. 2014-141488 filed on Jul. 9, 2014, the entire disclosure of which is incorporated herein by reference.

REFERENCE SIGNS LIST

1a Positive electrode active material layer
1b Positive electrode current collector
2 Separator
3a Negative electrode active material layer
3b Negative electrode current collector
4 Positive electrode terminal
5 Positive electrode tab
6 Negative electrode terminal
7 Negative electrode tab
8 Non-aqueous electrolyte
9 Casing
10 Secondary battery

The invention claimed is:

1. A non-aqueous electrolytic solution comprising a phosphinoamine-based compound represented by the following general formula (1):

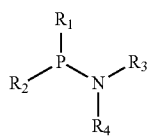

(1)

wherein $R_1$ and $R_2$ are each independently a hydrogen atom, a substituted or unsubstituted alkyl group, a substituted or unsubstituted alkenyl group, a substituted or unsubstituted cycloalkyl group, a substituted or unsubstituted aryl group, a substituted or unsubstituted heterocyclic group, a substituted or unsubstituted alkoxy group, or a hydroxy group; $R_3$ and $R_4$ are each independently a hydrogen atom, a substituted or unsubstituted alkyl group, a substituted or unsubstituted alkenyl group, a substituted or unsubstituted cycloalkyl group, a substituted or unsubstituted aryl group, a substituted or unsubstituted heterocyclic group, a substituted or unsubstituted alkoxy group, or a hydroxy group; $R_1$ and $R_2$ are optionally bonded via a single bond, an ether bond, or a hydrocarbon chain having 1 to 4 carbon atoms; and $R_3$ and $R_4$ are optionally bonded via a single bond, an ether bond, or a hydrocarbon chain having 1 to 4 carbon atoms.

2. The non-aqueous electrolytic solution according to claim 1, wherein the phosphinoamine-based compound is at least one selected from compounds (PN-1) to (PN-8) below:

(PN-1) 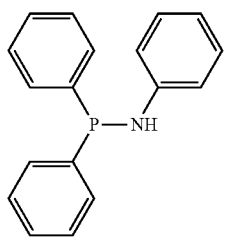

(PN-2) 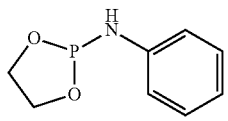

(PN-3) 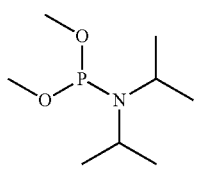

(PN-4) 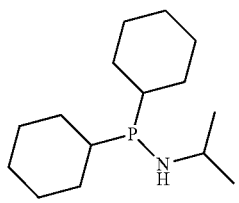

(PN-5) 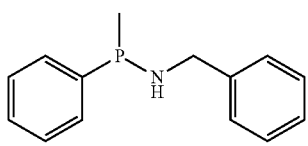

(PN-6) 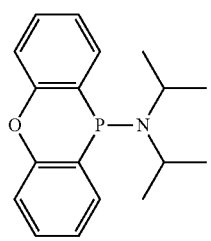

(PN-7) 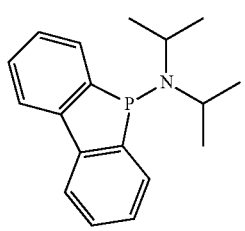

-continued (PN-8) 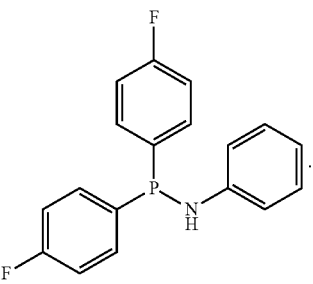

3. The non-aqueous electrolytic solution according to claim 1, wherein a content of the phosphinoamine-based compound in the non-aqueous electrolytic solution is 0.001 mass % or more and 5.0 mass % or less.

4. The non-aqueous electrolytic solution according to claim 1, further comprising an electrolyte salt and a non-aqueous electrolytic solvent.

5. A lithium ion secondary battery comprising the non-aqueous electrolytic solution according to claim 1.

6. The lithium ion secondary battery according to claim 5, comprising an electrode assembly in which a positive electrode and a negative electrode are disposed to face each other with a separator therebetween, and a casing enclosing the electrode assembly and the non-aqueous electrolytic solution.

7. The lithium ion secondary battery according to claim 5, wherein the positive electrode comprises a positive electrode active material that operates at an electric potential of 4.5 V or more versus lithium.

8. The lithium ion secondary battery according to claim 5, wherein the casing is a laminate film.

9. A lithium ion secondary battery comprising the non-aqueous electrolytic solution according to claim 2.

10. The lithium ion secondary battery according to claim 9, comprising an electrode assembly in which a positive electrode and a negative electrode are disposed to face each other with a separator therebetween, and a casing enclosing the electrode assembly and the non-aqueous electrolytic solution.

11. The lithium ion secondary battery according to claim 9, wherein the positive electrode comprises a positive electrode active material that operates at an electric potential of 4.5 V or more versus lithium.

12. The lithium ion secondary battery according to claim 9, wherein the casing is a laminate film.

13. A lithium ion secondary battery comprising the non-aqueous electrolytic solution according to claim 3.

14. The lithium ion secondary battery according to claim 13, comprising an electrode assembly in which a positive electrode and a negative electrode are disposed to face each other with a separator therebetween, and a casing enclosing the electrode assembly and the non-aqueous electrolytic solution.

15. The lithium ion secondary battery according to claim 13, wherein the positive electrode comprises a positive electrode active material that operates at an electric potential of 4.5 V or more versus lithium.

16. The lithium ion secondary battery according to claim 13, wherein the casing is a laminate film.

17. A lithium ion secondary battery comprising the non-aqueous electrolytic solution according to claim 4.

18. The lithium ion secondary battery according to claim 17, comprising an electrode assembly in which a positive electrode and a negative electrode are disposed to face each other with a separator therebetween, and a casing enclosing the electrode assembly and the non-aqueous electrolytic solution.

19. The lithium ion secondary battery according to claim 17, wherein the positive electrode comprises a positive electrode active material that operates at an electric potential of 4.5 V or more versus lithium.

20. The lithium ion secondary battery according to claim 17, wherein the casing is a laminate film.

* * * * *